US012138440B2

(12) United States Patent
Schilling et al.

(10) Patent No.: US 12,138,440 B2
(45) Date of Patent: Nov. 12, 2024

(54) MANAGING PUMP SPEED WHEN POWER CONSTRAINED IN A FULLY IMPLANTED LVAD SYSTEM

(71) Applicant: Medtronic, Inc., Minneapolis, MN (US)

(72) Inventors: Eric A. Schilling, Ham Lake, MN (US); Joel B. Artmann, Elk River, MN (US); Jason C. Lee, Edina, MN (US); David I. Siegfried, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 687 days.

(21) Appl. No.: 17/363,065

(22) Filed: Jun. 30, 2021

(65) Prior Publication Data

US 2022/0032038 A1     Feb. 3, 2022

Related U.S. Application Data

(60) Provisional application No. 63/059,333, filed on Jul. 31, 2020.

(51) Int. Cl.
*A61M 60/873*     (2021.01)
*A61M 60/178*     (2021.01)
*A61M 60/546*     (2021.01)
*A61M 60/592*     (2021.01)
*A61M 60/876*     (2021.01)

(52) U.S. Cl.
CPC ........ *A61M 60/873* (2021.01); *A61M 60/178* (2021.01); *A61M 60/546* (2021.01); *A61M 60/592* (2021.01); *A61M 60/876* (2021.01); *A61M 2205/04* (2013.01)

(58) Field of Classification Search
CPC .............. A61M 60/873; A61M 60/546; A61M 60/876; A61M 60/178; A61M 60/592; A61M 2205/04
USPC ........................................................ 600/16
See application file for complete search history.

(56) References Cited

U.S. PATENT DOCUMENTS

| 5,613,935 | A | 3/1997 | Jarvik |
| 6,149,683 | A * | 11/2000 | Lancisi ............... A61M 60/585 600/16 |
| 7,997,854 | B2 | 8/2011 | LaRose et al. |
| 8,096,935 | B2 | 1/2012 | Sutton et al. |
| 8,419,609 | B2 | 4/2013 | Shambaugh, Jr. et al. |
| 8,620,447 | B2 | 12/2013 | D'Ambrosio et al. |

(Continued)

OTHER PUBLICATIONS

International Search Report and Written Opinion of International Application No. PCT/US2021/041348, dated Oct. 11, 2021, 12 pp.

*Primary Examiner* — Erin M Piateski
(74) *Attorney, Agent, or Firm* — Shumaker & Sieffert, P.A.

(57) ABSTRACT

A method of managing a speed of implantable blood pump. The implantable blood pump is in communication with an internal battery and a transcutaneous energy transfer system (TETS). The method includes starting the pump at a programmed set speed. The speed of the pump is decreased from the programmed set speed to a minimum set speed if either a capacity of the internal battery is less than a predetermined reserve level and TETS power is unavailable, or there is insufficient TETS power to maintain the programmed set speed. The speed of the pump is progressively decreased from the programmed set speed if there is insufficient power to maintain the programmed set speed.

18 Claims, 3 Drawing Sheets

(56) References Cited

U.S. PATENT DOCUMENTS

| | | |
|---|---|---|
| 9,849,224 B2 | 12/2017 | Angwin et al. |
| 2007/0197854 A1* | 8/2007 | Marseille ............ A61M 60/531 600/16 |
| 2014/0371849 A1 | 12/2014 | Orejola et al. |
| 2015/0290374 A1* | 10/2015 | Bourque ............. A61M 60/422 600/17 |
| 2015/0290375 A1* | 10/2015 | Angwin ............. A61M 60/216 600/16 |

* cited by examiner

MANAGING PUMP SPEED WHEN POWER CONSTRAINED IN A FULLY IMPLANTED LVAD SYSTEM

CROSS-REFERENCE TO RELATED APPLICATION

This application claims the benefit of U.S. Application Ser. No. 63/059,333, filed Jul. 31, 2020.

FIELD

The present technology is generally related to implantable blood pumps, and in particular managing a speed of the blood pump when power is constrained.

BACKGROUND

With the advent of transcutaneous energy transfer systems (TETS) for implantable blood pumps increases the specter that power provided to the implantable blood pump may be constrained. For example, low internal battery power, misalignment of the coils of the TETS in the absence of internal battery power, thrombus, or transient power demands, each may constrain available power to the blood pump.

SUMMARY

The techniques of this disclosure generally relate to implantable blood pumps, and in particular managing a speed of the blood pump when power is constrained.

In one aspect, the present disclosure provides a method of managing a speed of implantable blood pump. The implantable blood pump is in communication with an internal battery and a transcutaneous energy transfer system (TETS). The method includes starting the pump at a programmed set speed. The speed of the pump is decreased from the programmed set speed to a minimum set speed if either a capacity of the internal battery is less than a predetermined reserve level and TETS power is unavailable, or there is insufficient TETS power to maintain the programmed set speed. The speed of the pump is progressively decreased from the programmed set speed if there is insufficient power to maintain the programmed set speed.

In another aspect of this embodiment, if the capacity of the internal battery is greater than the predetermined reserve level or TETS power is available, and there is sufficient power headroom, the method further includes progressively increasing the speed of the pump from the minimum set speed to the programmed set speed.

In another aspect of this embodiment, if the programmed set speed cannot be achieved with available power, the method further includes decreasing the speed of the pump to the minimum set speed after progressively increasing the speed of the pump from the minimum set speed.

In another aspect of this embodiment, if power is sufficient to maintain the minimum set speed, the method further includes increasing the speed of the pump to the programmed set speed after progressively decreasing the speed of the pump from the minimum set speed.

In another aspect of this embodiment, if the pump speed is less than a critical cutoff speed following progressively decreasing the speed of the pump, the method further includes acknowledging that the pump has stopped.

In another aspect of this embodiment, the method further includes attempting to restart the pump after the pump has stopped.

In another aspect of this embodiment, the pump is in communication with an implanted controller and wherein the implanted controller includes the internal battery.

In another aspect of this embodiment, the internal battery is in communication with an internal coil of the TETS.

In another aspect of this embodiment, the internal coil of the TETS is in communication with an external coil of the TETS, the external coil being further in communication with a power source.

In another aspect of this embodiment, the power source is one from the group consisting of wall power and a battery.

In one aspect, a control circuit for controlling a speed of an implantable blood pump, the control circuit being in communication with an internal battery and a transcutaneous energy transfer system (TETS), includes processing circuitry configured to start the pump to a programmed set speed. The speed of the pump is decreased from the programmed set speed to a minimum set speed if either a capacity of the internal battery is less than a predetermined reserve level and TETS power is unavailable, or there is insufficient power headroom. The speed of the pump is progressively decreased from the programmed set speed if there is insufficient power to maintain the minimum set speed.

In another aspect of this embodiment, if the power level of the internal battery is greater than the predetermined reserve level or TETS power is available, and there is sufficient power headroom, the processing circuitry is further configured to progressively increase the speed of the pump from the minimum set speed to the programmed set speed.

In another aspect of this embodiment, if the programmed set speed cannot be achieved with available power, the processing circuitry is further configured to decrease the speed of the pump to the minimum set speed after progressively increasing the speed of the pump from the minimum set speed.

In another aspect of this embodiment, if power is sufficient to maintain the minimum set speed, the processing circuitry is further configured to increase the speed of the pump to the programmed set speed after progressively decreasing the speed of the pump to the minimum set speed.

In another aspect of this embodiment, if the pump speed is less than a critical cutoff speed following progressively decreasing the speed of the pump, the processing circuitry is further configured to acknowledge the pump has stopped.

In another aspect of this embodiment, the processing circuitry is further configured to attempt to restart the pump after the pump has stopped.

In another aspect of this embodiment, the pump is in communication with an implanted controller and wherein the implanted controller includes the internal battery.

In another aspect of this embodiment, the internal battery is in communication with an internal coil of the TETS.

In another aspect of this embodiment, the internal coil of the TETS is in communication with an external coil of the TETS, the external coil being further in communication with a power source, and wherein the power source is one from the group consisting of wall power and a battery.

In one aspect, a control circuit for controlling a speed of an implantable blood pump, the control circuit being in communication with an internal battery and a transcutaneous energy transfer system (TETS), the control circuit includes processing circuitry configured to start the pump to a programmed set speed. The speed of the pump is decreased from the programmed set speed to a minimum set speed if either a capacity of the internal battery is less than a predetermined reserve level and TETS power is unavailable, or there is insufficient TETS power to maintain the programmed set speed. If there is insufficient power to maintain the minimum set speed, the speed of the pump is progressively decreased from the minimum set speed. If power is sufficient to maintain the minimum set speed, the speed of the pump is increased to the programmed set speed after progressively decreasing the speed of the pump from the minimum set speed. If the pump speed is less than a critical cutoff speed following progressively decreasing the speed of the pump, the pumped is turned off.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
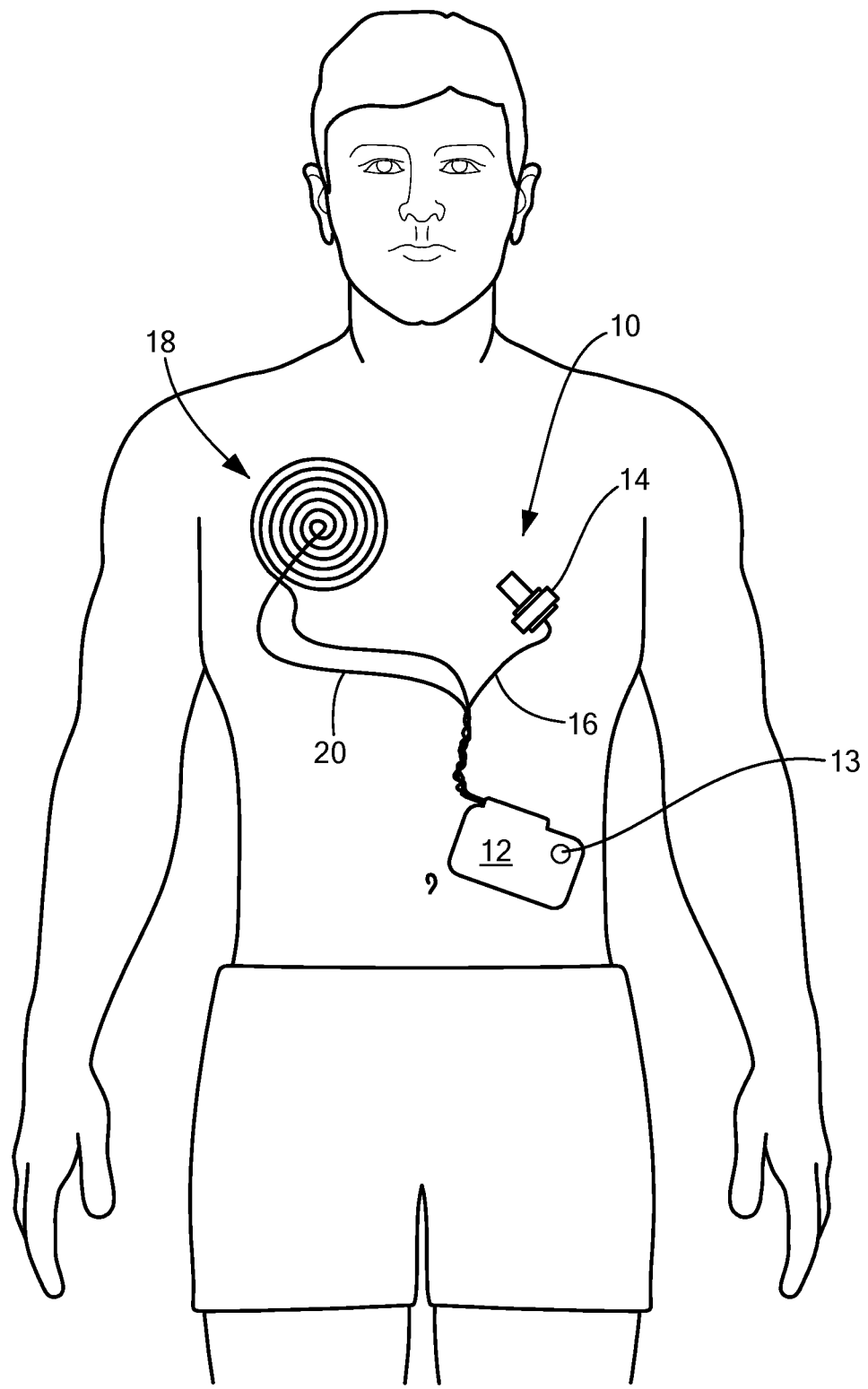
FIG. 1 is an internal system view of an implantable blood pump with a TETS receiver source constructed in accordance with the principles of the present application.
Figure 2:
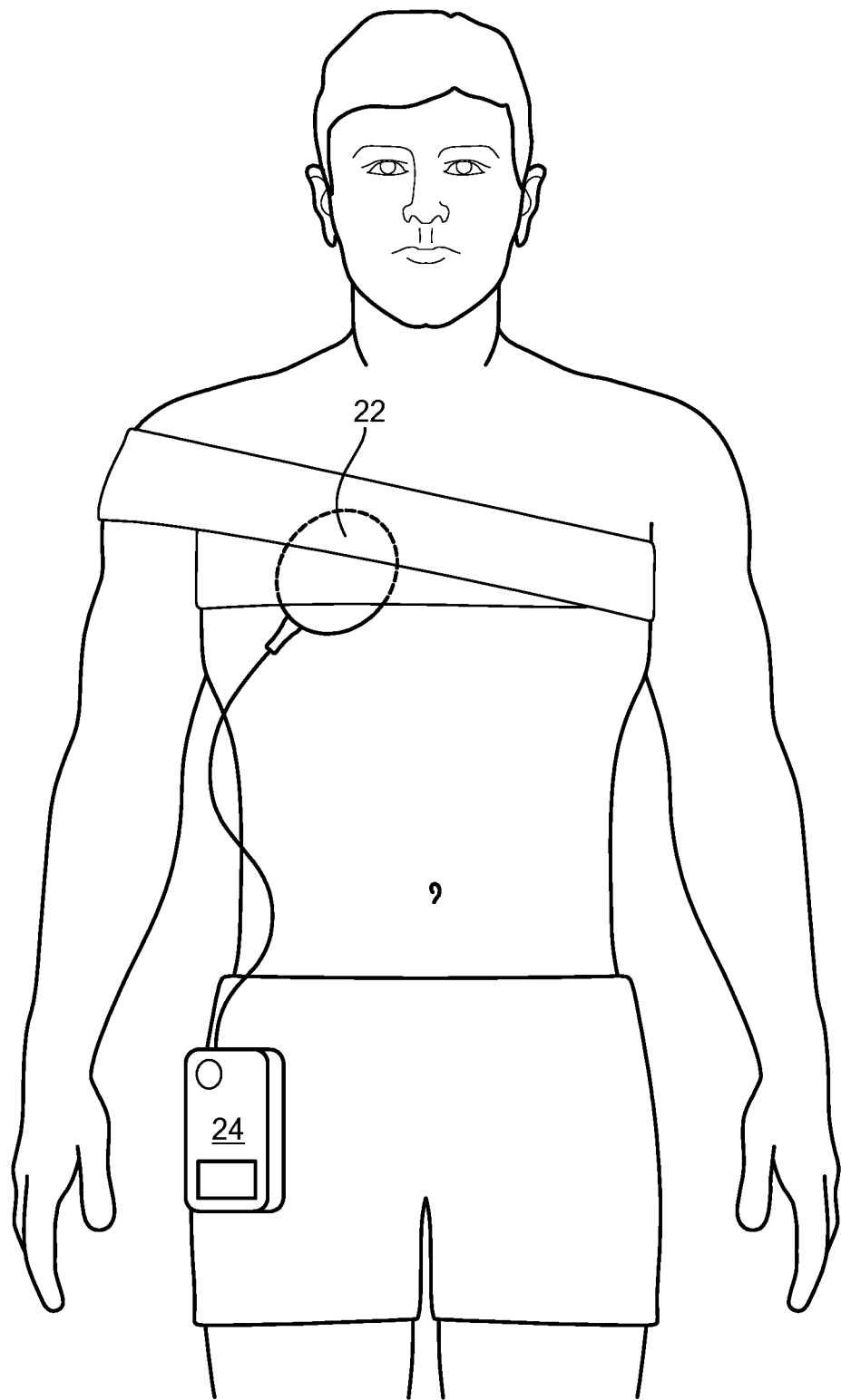
FIG. 2 is an external view of a TETS transmitter and a controller of the system shown in FIG. 1.

Referring now to the drawings in which like reference designators refer to like elements there is shown in FIGS. 1 and 2 an exemplary transcutaneous energy transfer system ("TETS") constructed in accordance with the principles of the present application and designated generally as "10." The TETS 10 may be fully implantable within a patient, whether human or animal, which is to say there are no percutaneous connections between the implanted components of the TETS 10 and the components outside of the body of the patient. In the configuration shown in FIG. 1, the TETS 10 includes an internal controller 12 implanted within the body of the patient. The internal controller 12 includes a control circuit having processing circuitry configured to control operation of an implantable blood pump 14. The internal controller 12 may include an internal power source 13, configured to power the components of the controller and provide power to one or more implantable medical devices, for example, the implantable blood pump, such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997, 854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving or internal coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission or external coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient or wall power. In one configuration, the battery is configured to generate a radiofrequency signal for transmission of energy from the transmission coil 22 to the receiving coil 18. The receiving coil 18 may be configured for transcutaneous inductive communication with the transmission coil 22.

Figure 3:
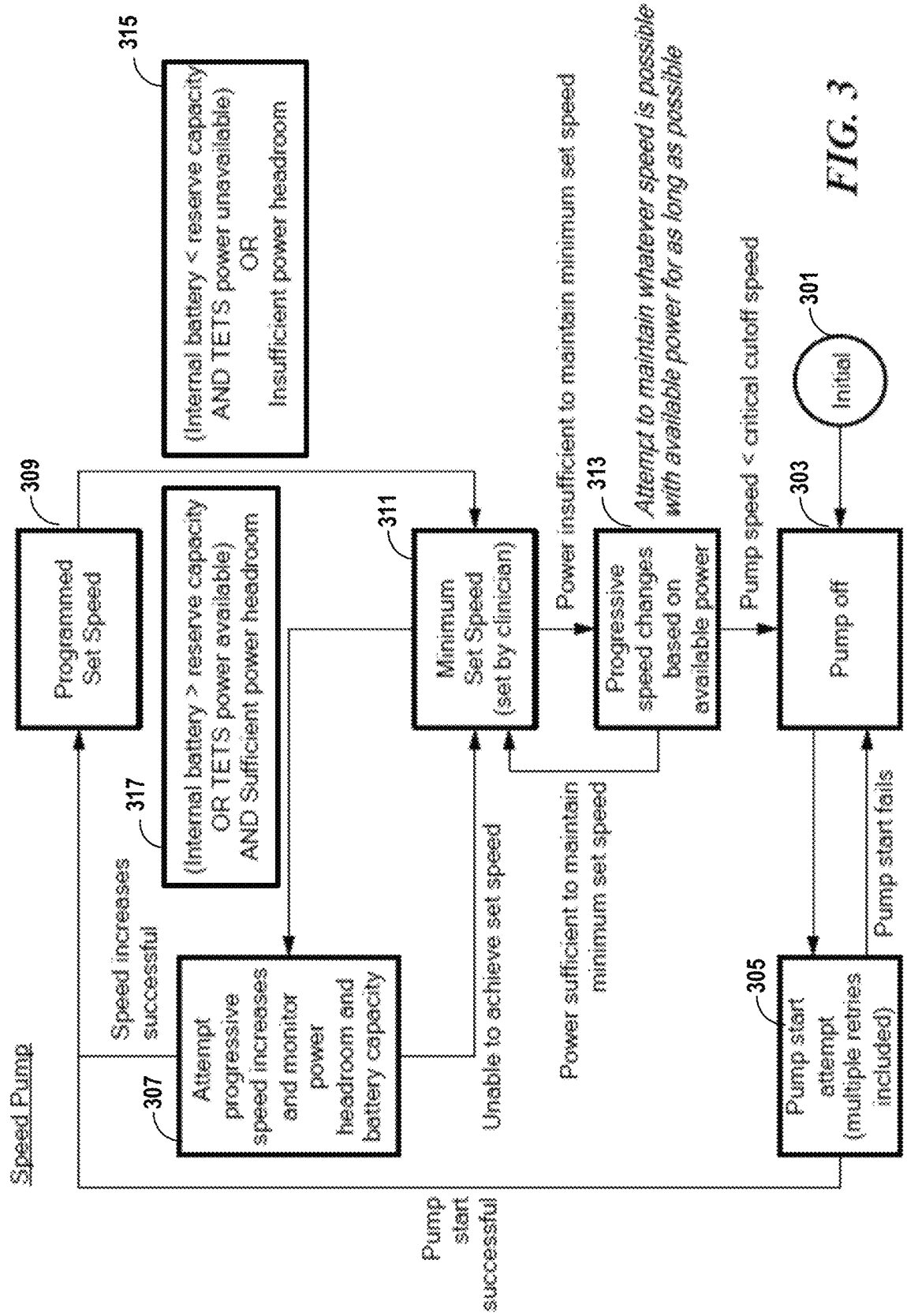
FIG. 3 is a flow chart showing a method of managing a speed of the blood pump when power is constrained.

Referring now to FIG. 3, where an exemplary method of managing a speed of implantable blood pump 14 is shown. The method includes starting the pump 14 (301). That is initially the pump is turned off (303) and the control circuit of the controller 12 is configured to start the pump 12 and to bring the speed of the pump 14 to a programmed set speed (309), for example, 2400-3200 RPM. If the pump 14 does not initially start, the control circuit is configured to make multiple attempts to start the pump (305). The set speed may be programmed by the clinician or may be default value preprogrammed into the controller 12 (309). If either a power level of the internal battery 13 is less than a predetermined reserve level and TETS power is unavailable, or there is insufficient power headroom (315), the control circuit is further configured to decrease the speed of the pump from the programmed set speed to a minimum set speed (311), for example, 1800-2200 RPM. For example, the power headroom may be a predefined threshold related to, for example, a difference between the power available and the power used. In other configurations, power headroom may be an absolute threshold related to voltage, current, or power supplied to pump 14. In still other configurations, power headroom be a threshold based on a percentage of the pulse width modulated duty cycle of a signal provided to the pump 14. For example, if common power transients typically result in a 10% increase in the PWM duty cycle, the threshold for "insufficient power headroom" could be a PWM duty cycle of 90%.

The controller 12 may include a minimum set speed (311) at which the pump 14 operates while providing sufficient blood flow. This minimum set speed may be programmed into the controller 12 or set by a clinician (311). If the power level of the internal battery 13 is greater than the predetermined reserve level or TETS power is available, and there is sufficient power headroom (317), then the control circuit is configured to attempt to progressively increase the speed of the pump (307) from the minimum set speed (311) back to the programmed set speed (309). The speed increases may be ramped up or stepped up from the minimum set speed and may occur after a predetermined amount of time or immediately. If the pump 14 is unable to reach the programmed set speed, the control circuit reduces the speed of the pump 14 back to the minimum set speed (311). If there is insufficient power to maintain the minimum set speed, the control circuit progressively decreases the speed of the pump 14 from the minimum set speed to attempt to maintain whatever speed is possible with minimum power (313). The speed decreases may be ramped down or stepped down from the minimum set speed and may occur after a predetermined amount of time or immediately. If the pump speed is less than a critical cutoff speed, for example, 900-1200 RPM following progressively decreasing the speed of the pump 14, the control circuit is configured to turn off the pump 14 (303). Moreover, the pump 14 may be shut off at any one of these stages due to complete loss of power, faults, or via explicit programming commands.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of managing a speed of implantable blood pump, the implantable blood pump being in communication with an internal battery and a transcutaneous energy transfer system (TETS), the method comprising:
   starting the pump at a programmed set speed;
   decreasing the speed of the pump from the programmed set speed to a minimum set speed if either a capacity of the internal battery is less than a predetermined reserve level and TETS power is unavailable, or there is insufficient TETS power to maintain the programmed set speed;
   progressively decreasing the speed of the pump from the minimum set speed to maintain a speed below the minimum set speed that is supported by available power if there is insufficient power to maintain the minimum set speed; and
   stopping the pump if the speed below the minimum set speed is less than a critical cutoff speed.

2. The method of claim 1, wherein if the capacity of the internal battery is greater than the predetermined reserve level or TETS power is available, and there is sufficient TETS power headroom, the method further includes progressively increasing the speed of the pump from the minimum set speed to the programmed set speed.

3. The method of claim 1, wherein if power is sufficient to maintain the minimum set speed, the method further includes increasing the speed of the pump to the minimum set speed after progressively decreasing the speed of the pump from the programmed set speed.

4. The method of claim 1, further including attempting to restart the pump after it has stopped.

5. The method of claim 1, wherein the pump is in communication with an implanted controller and wherein the implanted controller includes the internal battery.

6. The method of claim 5, wherein the internal battery is in communication with an internal coil of the TETS.

7. The method of claim 6, wherein the internal coil of the TETS is in communication with an external coil of the TETS, the external coil being further in communication with a power source.

8. The method of claim 7, wherein the power source is one from the group consisting of wall power and a battery.

9. A control circuit for controlling a speed of an implantable blood pump, the control circuit being in communication with an internal battery and a transcutaneous energy transfer system (TETS), the control circuit comprising:
   processing circuitry configured to:
      start the pump to a programmed set speed;
      decrease the speed of the pump from the programmed set speed to a minimum set speed if either a capacity of the internal battery is less than a predetermined reserve level and TETS power is unavailable, or there is insufficient power headroom;
      progressively decrease the speed of the pump from the minimum set speed to maintain a speed below the minimum set speed that is supported by available power if there is insufficient power to maintain the minimum set speed; and
      stop the pump if the speed below the minimum set speed is less than a critical cutoff speed.

10. The control circuit of claim 9, wherein if the capacity of the internal battery is greater than the predetermined reserve level or TETS power is available, and there is sufficient power headroom, the processing circuitry is further configured to progressively increase the speed of the pump from the minimum set speed to the programmed set speed.

11. The control circuit of claim 9, wherein if power is sufficient to maintain the minimum set speed, the processing circuitry is further configured to increase the speed of the pump to the minimum set speed after progressively decreasing the speed of the pump from to the programmed set speed.

12. The control circuit of claim 9, wherein the processing circuitry is further configured to attempt to restart the pump after the pump has stopped.

13. The control circuit of claim 9, wherein the pump is in communication with an implanted controller and wherein the implanted controller includes the internal battery.

14. The control circuit of claim 13, wherein the internal battery is in communication with an internal coil of the TETS.

15. The control circuit of claim 14, wherein the internal coil of the TETS is in communication with an external coil of the TETS, the external coil being further in communication with a power source, and wherein the power source is one from the group consisting of wall power and a battery.

16. A control circuit for controlling a speed of an implantable blood pump, the control circuit being in communication with an internal battery and a transcutaneous energy transfer system (TETS), the control circuit comprising:
   processing circuitry configured to:
      start the pump to a programmed set speed;
      decrease the speed of the pump from the programmed set speed to a minimum set speed if either a capacity of the internal battery is less than a predetermined reserve level and TETS power is unavailable, or there is insufficient TETS power to maintain the programmed set speed;
      if there is insufficient power to maintain the minimum set speed, progressively decrease the speed of the pump from the minimum set speed to maintain a speed below the minimum set speed that is supported by available power;
      if power is sufficient to maintain the minimum set speed, increase the speed of the pump to the minimum set speed after progressively decreasing the speed of the pump from the programmed set speed; and
      if the speed below the minimum set speed is less than a critical cutoff speed, stop the pump.

17. The method of claim 2, wherein the power headroom is a predefined threshold indicative of a difference between available power and a consumed power.

18. The control circuit of claim 10, wherein the power headroom is a predefined threshold indicative of a difference between available power and a consumed power.

* * * * *